(12) United States Patent
Jay-Robinson

(10) Patent No.: US 7,967,809 B2
(45) Date of Patent: Jun. 28, 2011

(54) SELF-SEALING ASSEMBLY FOR PREVENTING FLUID LEAKAGE FROM MEDICAL DEVICE

(75) Inventor: Tracy Ann Jay-Robinson, Jamaica Plain, MA (US)

(73) Assignee: OBP Corporation, Lawrence, MA (US)

( * ) Notice: Subject to any disclaimer, the term of this patent is extended or adjusted under 35 U.S.C. 154(b) by 219 days.

(21) Appl. No.: 12/128,419

(22) Filed: May 28, 2008

(65) Prior Publication Data

US 2009/0299336 A1  Dec. 3, 2009

(51) Int. Cl.
*A61M 5/00* (2006.01)
(52) U.S. Cl. ........................................................ 604/533
(58) Field of Classification Search .................. 604/164.01–170.03, 533
See application file for complete search history.

(56) References Cited

U.S. PATENT DOCUMENTS

| | | | |
|---|---|---|---|
| 4,649,904 A | 3/1987 | Krauter et al. | 128/6 |
| 4,655,752 A | 4/1987 | Honkanen et al. | 604/256 |
| 4,817,631 A * | 4/1989 | Schnepp-Pesch et al. | 600/566 |
| 4,966,588 A * | 10/1990 | Rayman et al. | 604/165.02 |
| 6,053,861 A | 4/2000 | Grossi | 600/154 |
| 6,254,529 B1 | 7/2001 | Ouchi | 600/154 |
| 6,551,282 B1 | 4/2003 | Exline et al. | 604/167.01 |
| 6,908,428 B2 | 6/2005 | Aizenfeld et al. | 600/123 |
| 7,226,411 B2 | 6/2007 | Akiba | 600/154 |
| 7,276,075 B1 * | 10/2007 | Callas et al. | 606/191 |
| 2006/0041189 A1 | 2/2006 | Vancaillie | 600/154 |
| 2006/0211992 A1 * | 9/2006 | Prosek | 604/167.06 |
| 2007/0161957 A1 | 7/2007 | Guenther et al. | 604/167.01 |
| 2007/0238928 A1 * | 10/2007 | Maseda et al. | 600/153 |

OTHER PUBLICATIONS

International Search Report for PCT/US09/45244 dated Jul. 13, 2009.

\* cited by examiner

*Primary Examiner* — Kevin C Sirmons
*Assistant Examiner* — Imani Hayman
(74) *Attorney, Agent, or Firm* — Bowditch & Dewey, LLP

(57) ABSTRACT

Self-sealing assemblies and methods of establishing a fluid-seal around a medical instrument are disclosed herein. An assembly for providing resistance to fluid leakage includes an introducer section having a mouth portion, a stem portion, and a longitudinal axis therebetween, wherein a diameter of the mouth portion decreases over a length of the mouth portion, and wherein a diameter of the stem portion remains substantially the same over a length of the stem portion; a transfer section having a proximal end and a distal end; and a self-sealing membrane at a junction between the stem portion and the proximal end of the transfer section, wherein the self-sealing membrane is composed of a single piece flexible elastomeric material, and wherein the diameter and the length of the stem portion and a thickness and a diameter of the self-sealing membrane provide structural integrity to the assembly resulting in the ability of the self-sealing membrane to resist fluid leakage prior to, during, and after the self-sealing membrane is punctured.

20 Claims, 5 Drawing Sheets

Auxiliary Instrument →

SELF-SEALING ASSEMBLY FOR PREVENTING FLUID LEAKAGE FROM MEDICAL DEVICE

RELATED APPLICATIONS

None.

FIELD

The embodiments disclosed herein relate to self-sealing assemblies for medical devices, and more particularly to self-sealing assemblies to prevent fluid leakage and backflow and methods of using self-sealing assemblies during a medical procedure.

BACKGROUND

Endoscopes are medical viewing instruments with capabilities of diagnostic (biopsy) or even therapeutic functions through special operative channels. Endoscopes now have widespread use in medicine and guide a myriad of diagnostic and therapeutic procedures including, but not limited to, arthroscopy, bronchoscopy, colonoscopy, colposcopy, cystoscopy, gastroscopy, hysteroscopy, laparoscopy, laryngoscopy, proctoscopy and thoracoscopy. For example, hysteroscopy is the inspection of the uterine cavity by endoscopy and allows for the diagnosis of intrauterine pathology and serves as a method for surgical intervention. Hysteroscopes are endoscopes that are used during hysteroscopy and are typically provided with at least one accessory channel which permits the introduction of various surgical auxiliary instruments, such as forceps, scissors or other specialized biopsy instruments. Such auxiliary instruments are introduced into the accessory channel through an inlet port. The inlet port is therefore a site of potential escape of blood and other bodily fluids (biomaterials), as well as introduced fluids, which may result in the leaking or spraying of medical personnel and equipment. These fluids may contain viruses and other biological agents that pose a risk to the personnel or that contaminate the equipment.

Because of the potential for the leakage of fluids, various types of valves, plugs and seals are typically placed at or near the inlet port. These plugs attempt to seal the tiny spaces around the auxiliary instrument where the potential for leakage is greatest, and are used to close off the inlet port when an auxiliary instrument is not in place. However, the current surgical plugs still have a tendency to leak, especially if multiple auxiliary instruments are used. Additionally, current surgical plugs can only be used with auxiliary instruments having a relatively narrow range of diameters. Current large diameter surgical valves do not close completely and require that the auxiliary instrument be left in place to maintain a seal. Current surgical valves require constant manipulation to maintain a seal around the auxiliary instrument without excessive friction. Between the time an auxiliary instrument is removed from the endoscope and the accessory-port valve is closed, blood or other bodily fluid can leak or spray from the port because the seal does not effectively self-close. This happens because the seal around the auxiliary instrument may be distorted by an instrument that previously passed through and stretched the aperture. These problems and shortcomings may be solved by the self-sealing assemblies of the present disclosure

SUMMARY

Self-sealing assemblies for the prevention of fluid leakage from a medical device and methods of using these assemblies during a medical procedure are disclosed herein. According to aspects illustrated herein, there is provided an assembly for providing resistance to fluid leakage that includes an introducer section having a mouth portion, a stem portion, and a longitudinal axis therebetween, wherein a diameter of the mouth portion decreases over a length of the mouth portion, and wherein a diameter of the stem portion remains substantially the same over a length of the stem portion; a transfer section having a proximal end and a distal end; and a self-sealing membrane at a junction between the stem portion and the proximal end of the transfer section, wherein the self-sealing membrane is composed of a single piece flexible elastomeric material, and wherein the diameter and the length of the stem portion and a thickness and a diameter of the self-sealing membrane provide structural integrity to the assembly resulting in the ability of the self-sealing membrane to resist fluid leakage prior to, during, and after the self-sealing membrane is punctured.

According to aspects illustrated herein, there is provided an assembly for providing resistance to fluid backflow that includes an outer circumferential surface having a proximal end, a distal end, and a middle region therebetween, wherein the middle region includes a proximal lip, a distal lip, and a cavity therebetween; and an inner surface having an introducer section, a transfer section, and a self-sealing membrane therebetween, wherein the introducer section is approximately funnel-shaped, having a first portion, a second portion, and a longitudinal axis therebetween, wherein a diameter of the first portion decreases over a first length, and wherein a diameter of the second portion remains substantially the same over a second length, wherein the transfer section has a proximal end, a distal end, and a longitudinal axis therebetween, and wherein the self-sealing membrane is composed of a single piece flexible elastomeric material having a thickness such that the self-sealing membrane extends from the second portion of the introducer section into the transfer section when pressure is applied to the self-sealing membrane.

According to aspects illustrated herein, there is provided a method for establishing a fluid-seal around a medical instrument that includes attaching an assembly to an accessory channel of a medical device, wherein the assembly comprises an introducer section, a transfer section, and a self-sealing membrane therebetween, wherein the introducer section is approximately funnel-shaped, having a first portion, a second portion, and a longitudinal axis therebetween, wherein a diameter of the first portion decreases over a first length, and wherein a diameter of the second portion remains substantially the same over a second length, wherein the self-sealing membrane is composed of a single piece flexible elastomeric material, and wherein the transfer section is attached to the accessory channel of the medical device; introducing the medical instrument into the introducer section of the assembly such that the first portion guides the medical instrument into the second portion, and the second portion contacts and squeezes the medical instrument as the medical instrument passes through the length of the second portion; exerting pressure on the self-sealing membrane by the medical instrument resulting in the self-sealing membrane stretching in a direction from a proximal end of the transfer section towards a distal end of the transfer section; and creating a hole in the self-sealing membrane such that the medical instrument engages an entire inner surface of the hole as the medical instrument passes through the self-sealing membrane and into the transfer section, resulting in the fluid-seal around the medical instrument.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A shows a perspective view of the self-sealing assembly. FIG. 1B shows a perspective cross-sectional view of the self-sealing assembly. FIG. 1C shows a cross-sectional view of the self-sealing assembly.

FIG. 2A shows a top view of the self-sealing assembly. FIG. 2B shows a bottom view of the self-sealing assembly.

FIG. 3A shows a side view of the Luer-lock adaptor and the self-sealing assembly prior to engagement. FIG. 3B shows a side view of the Luer-lock adaptor and the self-sealing assembly during engagement. FIG. 3C shows a side view of the Luer-lock adaptor and the self-sealing assembly after engagement.

FIG. 4A shows a side view of the self-sealing assembly prior to engagement to the hysteroscope. FIG. 4B shows a side view of the self-sealing assembly after engagement to the hysteroscope.

FIG. 5A shows a side view of the self-sealing assembly prior to engagement to the hysteroscope. FIG. 5B shows a side view of the self-sealing assembly during engagement to the hysteroscope. FIG. 5C shows a side view of the self-sealing assembly after engagement to the hysteroscope.

DETAILED DESCRIPTION

Figure 1A:
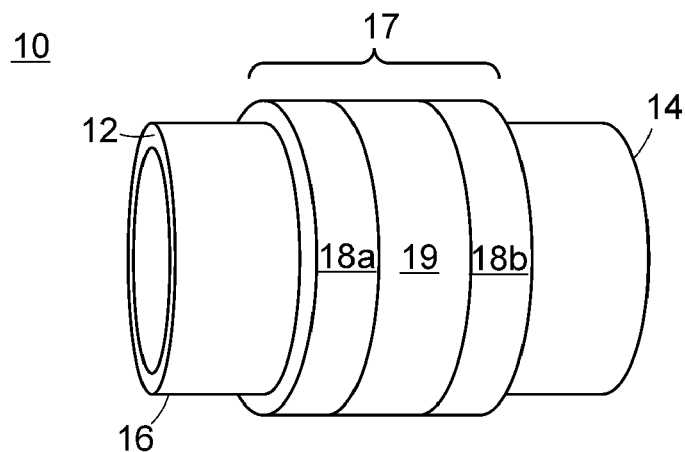
FIGS. 1A, 1B and 1C show an embodiment of a self-sealing assembly of the present disclosure.

Self-sealing assemblies that are capable of preventing fluid leakage and backflow are disclosed herein. Methods of using these self-sealing assemblies in conjunction with medical instruments during a medical procedure are also disclosed. In an embodiment, the self-sealing assemblies of the present disclosure are provided for single-use and are disposable. The self-sealing assemblies are designed to be placed directly over an inlet port of an accessory channel of a medical device or alternatively, may be engaged to an adaptor which is attached to the inlet port of the accessory channel. For example, the self-sealing assemblies may be engaged with a Luer-lock adaptor, a ball-in-socket adaptor, or a Tuohy Borst adaptor.

As used herein, the term "endoscope" generally refers to a medical device having a light attached that is used to look inside a body cavity or organ. The self-sealing assemblies of the present disclosure may be used with various types of endoscopes including, but not limited to, hysteroscopes and resectoscopes. In an embodiment, the self-sealing assemblies of the present disclosure are used in conjunction with a hysteroscope during an operative hysteroscopy procedure. It should be understood that the self-sealing assemblies of the present disclosure can be used with any type of medical device for which a fluid-seal is desired, such as various scopes and catheters.

As used herein, the term "hysteroscope" refers to a thin telescope for minimally invasive operative access to the interior of a subject's uterus. A typical hysteroscope used during an operative hysteroscopy procedure includes at least one "accessory channel" or "operative channel", which is a lumen for the insertion of auxiliary instruments or distention media. To accomplish insufflation (distention) of a subject's uterus, a gas feed line may be attached to a gas port on the hysteroscope which feeds into the operative channel. By using a hysteroscope having one operative channel for gas insufflation and for auxiliary instrument (e.g., forceps) insertion, the insertion arm of the hysteroscope may be minimized, permitting comfortable and easy uterine access as well as access without inducing dilation.

As used herein, the term "self-sealing" refers to a feature of any one of the assemblies of the presently disclosed embodiments. The presently disclosed assemblies include a flexible elastomeric membrane having a thickness to a diameter ratio such that the membrane is capable of sealing itself after being punctured.

As used herein, the term "resistance to fluid leakage" refers to a feature of any one of the self-sealing assemblies of the presently disclosed embodiments where the leakage of fluid from a medical device is minimized.

As used herein, the term "backflow" refers to the reversal of fluid or biomaterial flow from a medical device. Backflow is generally undesirable in medical procedures.

As used herein, the term "auxiliary instrument" refers to an instrument that may be inserted into any one of the self-sealing assemblies of the presently disclosed embodiments any manipulated during a medical procedure. Examples of auxiliary instruments include, but are not limited to, catheters, guide wires, forceps, scissors, cystoscopic graspers, hysteroscopic graspers, monopolar and bipolar electrodes, ureteral stints, morcellation devices, electrosurgical probes, stone baskets and retrievers.

As used herein, the term "approximately funnel-shaped" denotes a three-dimensional cylinder that has a diameter at one end larger than the other, i.e., in the shape of a cone.

As used herein, the term "elastomeric material" refers to a polymer with the property of elasticity. Silicone elastomer is a polymer that has a "backbone" of silicone-oxygen linkages. "Silastic" refers to the trademark name registered by Dow Corning Corporation for polymeric silicone elastomeric substances that have the properties of rubber but are biologically inert. In an embodiment, the medical assemblies of the present disclosure are fabricated from Silastic®. In an embodiment, the Silastic® is a GP 500 silicone rubber manufactured from Dow Corning Corporation.

As used herein, the term "hugging" refers to a feature provided by any one of the self-sealing assemblies of the presently disclosed embodiments. The presently disclosed self-sealing assemblies include an introducer section having a narrow stem portion that is capable of completely contacting, surrounding, and gently squeezing an auxiliary instrument as it passes through the stem portion. Such hugging prevents fluid, even under pressure, from extruding around the auxiliary instrument as it passes through the stem portion of the self-sealing assembly.

As used herein, the term "structural integrity" refers to a feature provided by an assembly of the presently disclosed embodiments prior to, during, and after puncture by a medical instrument, as well as after the medical instrument is removed from the assembly. When an assembly of the presently disclosed embodiments is placed on a hysteroscope for use during a medical procedure, prior to being punctured by an auxiliary medical instrument, the self-sealing membrane of the assembly provides resistance to fluid backflow out of the assembly. The self-sealing membrane is fabricated from a single-piece material that blocks fluid from passing through the self-sealing membrane. After being punctured by the auxiliary instrument, the structural design of the internal portions of the assembly provides the ability to resist fluid backflow. The assembly hugs the auxiliary instrument and surrounds and supports the auxiliary instrument. During use, the structural design of the internal portions of the assembly provides the ability to resist fluid backflow. The self-sealing membrane mimics any lateral movement imparted on the small diameter internal portions leading up to the self-sealing membrane by the auxiliary instrument, and thus any lateral movement will be transferred to the self-sealing membrane such that a center of the self-sealing membrane is always aligned with a center of the auxiliary instrument. This "floating membrane" design insures leakage is prevented during any lateral movement by the auxiliary instrument. A ratio of the thickness of the self-sealing membrane to the diameter of the self sealing membrane is chosen such that the self sealing membrane provides resistance to fluid leakage even after the auxiliary instrument is removed from the self-sealing membrane. The self-sealing membrane will remain substantially closed even if fluid or gas pressure is present in the assembly.

As shown in the perspective view of FIG. 1A, a self-sealing assembly 10 of the present disclosure has a tubular shape and includes a proximal end 12, a distal end 14 and a middle region 17 therebetween. In an embodiment, a longitudinal length of the assembly 10 is from about 15 mm to about 18 mm. The proximal end 12 of the assembly 10 is that end into which an auxiliary instrument would be inserted, while the distal end 14 of the assembly 10 is that end that would be placed over an inlet port to an accessory channel on a medical device. The assembly 10 may be attached directly to the inlet port, or alternatively, may be engaged with an adaptor that is attached to a fitting on the inlet port, as will be described in more detail below. Middle region 17 has a proximal lip 18a, a distal lip 18b, and a cavity 19 therebetween. The middle region 17 extends outward beyond an outer circumferential surface 16 of the assembly 10. In an embodiment, an elastic band is wrapped around the assembly 10 such that it is housed within the cavity 19. The elastic band may be fabricated from different colors which represent a diameter of an internal feature of the assembly 10, as will be described in more detail below.

Figure 1B:
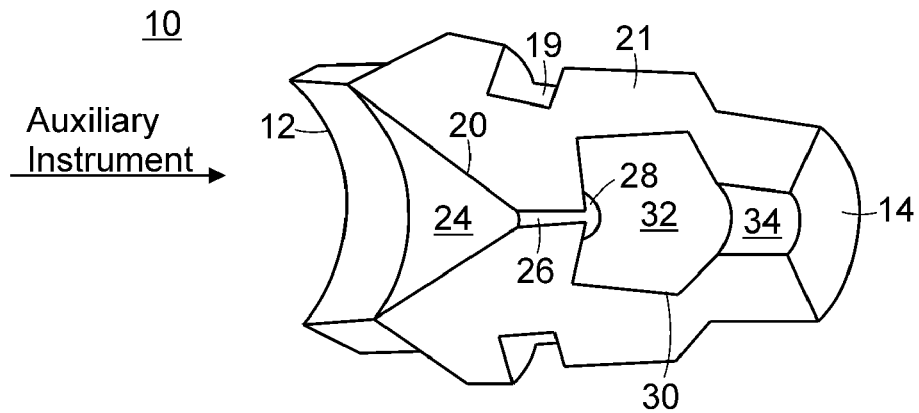

FIG. 1B shows a perspective cross-sectional view of the assembly 10. The assembly 10 includes a body 21 having two longitudinally adjacent sections, an introducer section 20 and a transfer section 30, separated from one another by a flexible membrane 28. The introducer section 20 has a proximal section 24, a distal section 26, and a longitudinal axis therebetween. In an embodiment, the distal section 26 is aligned centrally with respect to the proximal section 24. In an embodiment, the introducer section 20 is approximately funnel-shaped, having a wide conical shaped mouth as the proximal section 24 for receiving an auxiliary instrument, and a narrow stem shaped distal section 26 for contacting and squeezing the auxiliary instrument as the instrument passes through the distal section 26. The conical shaped mouth portion 24 has a diameter that gradually decreases over a length of the mouth portion 24, such that a first or initial diameter at a proximal end of the mouth portion 24 is larger than a second or final diameter at a distal end of the mouth portion 24. The funnel-shape of the introducer section 20 is designed in such a way that the auxiliary instrument may be placed within the assembly 10 with ease, and the auxiliary instrument may be guided and squeezed towards the membrane 28. The stem portion 26 is designed to have a desired length and a desired diameter such that the auxiliary instrument is squeezed as the instrument is directed through the length of the stem portion 26 towards the membrane 28. In an embodiment, a diameter of the stem portion 26 is constant along the entire length of the stem portion 26. In an embodiment, the diameter of the stem portion 26 gradually decreases along the length of the stem portion 26. In an embodiment, a length of the longitudinal axis of the introducer section 20 ranges from about 3 mm to about 5 mm. In an embodiment, the mouth portion 24 has an initial diameter ranging from about 7 mm to about 9 mm. In an embodiment, the mouth portion 24 has a final diameter ranging from about 0.6 mm to about 2 mm. In an embodiment, a diameter of the stem portion 26 is from about 0.6 mm to about 2 mm. In an embodiment, the length of the stem portion 26 is from about 3 mm to about 4 mm.

The transfer section 30 has a proximal end 32, a distal end 34, and a longitudinal axis therebetween. The transfer section 30 is that portion of the assembly 10 that attaches directly, or indirectly to the inlet port on the medical device, as well as that portion of the assembly 10 in which the auxiliary instrument exits the assembly 10 and enters the accessory channel of the medical device. The transfer section 30 is capable of stretching to fit around various different adaptor pieces, as well as around the inlet port of the medical device. The transfer section 30 terminates at the distal end 14 of the assembly 10. In an embodiment, the proximal end 32 of the transfer section 30 is larger than the distal end 34 of the transfer section 30. In an embodiment, a length of the longitudinal axis of the transfer section of the transfer section 30 ranges from about 5 mm to about 9 mm.

The flexible membrane 28 is at a junction between the stem portion 26 and the proximal end 32 of the transfer section 30. The membrane 28 extends from and covers an entire opening created at the junction, therefore a diameter of the membrane 28 is substantially the same as the diameter of the stem portion 26. In an embodiment, a thickness of the membrane 28 extends from the stem portion 26 and into the transfer section 30. In an embodiment, the membrane 28 is an extension of outer walls of the stem portion 26 to form the covering of the opening created at the junction. In an embodiment, the membrane 28 is a separate piece of material that has been added to or extends from the assembly at the junction between the stem portion 26 and the proximal end 32 of the transfer section 30. The membrane 28 is designed to have a desired thickness, such that the membrane 28 is capable of stretching to a maximum convexity when pressure is applied to the membrane 28 by the auxiliary instrument and before being pierced by the auxiliary instrument. Prior to the introduction of the auxiliary instrument through the assembly 10, the membrane 28 is fully in-tact, meaning that there are no holes or perforations in the membrane 28. Therefore, when the assembly 10 is placed over the inlet port of the medical device, such as a hysteroscope, there is no need for extra valves or fittings to be placed on the hysteroscope for the prevention of fluid leakage out of the port. The fully in-tact membrane 28 provides this leakage protection. In an embodiment, the membrane 28 has a diameter ranging from about 0.6 mm to about 2 mm. In an embodiment, the membrane 28 has a thickness ranging from about 0.3 mm to about 2 mm. A ratio of the thickness of the self-sealing membrane 28 to the diameter of the self sealing membrane 28 is chosen such that the self sealing membrane 28 remains substantially closed after being pierced by an auxiliary instrument, even if fluid or gas pressure is present in the assembly 10. Even after the auxiliary instrument is removed from the membrane 28, the membrane 28 is capable of recovering to substantially an original shape. This substantial original shape will prevent leakage even though the membrane 28 has been pierced and pressure still exists in the assembly 10.

Figure 1C:
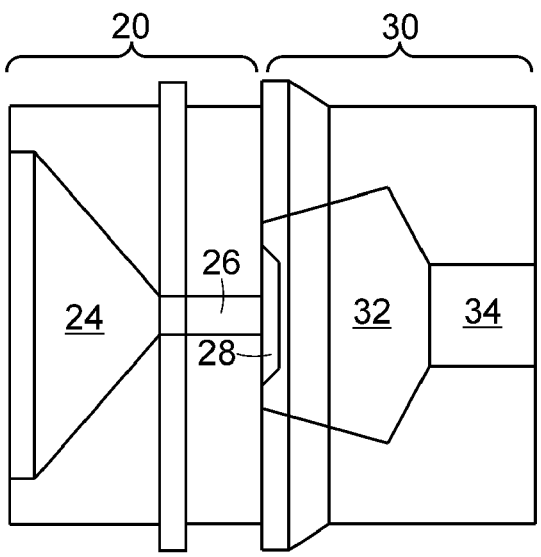

FIG. 1C shows a cross-sectional view of the assembly 10. In an embodiment, the length of the stem portion 26 is less than the length of the mouth portion 24. In an embodiment, the length of the stem portion 26 is about 9/10 the length of the mouth portion 24. In an embodiment, the length of the stem portion 26 is about 3.5 mm. In an embodiment, the length of the mouth portion 24 is about 3.9 mm. In an embodiment, the diameter of the mouth portion 24 gradually decreases such that an initial diameter of the mouth portion 24 is about 10 times as much as a final diameter of the mouth portion 24 and a diameter of the stem portion 26. In an embodiment, the diameter of the mouth portion 24 gradually decreases such that an initial diameter of the mouth portion 24 is about 5 times as much as a final diameter of the mouth portion 24 and a diameter of the stem portion 26. In an embodiment, the initial diameter of the mouth portion 24 is in a range of about 6 mm to about 12 mm. In an embodiment, the final diameter of the mouth portion 24 is in a range of about 0.6 mm to about 2 mm. In an embodiment, the diameter of the stem portion 26 is in a range of about 0.6 mm to about 2 mm. In an embodiment, the length of the transfer section 30 is longer than the length of the introducer section 20. In an embodiment, the length of the introducer section 20 is about 7.5 mm. In an embodiment, the length of the transfer section 30 is about 8 mm. In an embodiment, the diameter of the membrane 28 is in a range of about 0.6 mm to about 2 mm. In an embodiment, the thickness of the membrane 28 is about 5 times less than the length of the stem portion 26. In an embodiment, the thickness of the membrane 28 is about 0.9 mm. In an embodiment, the thickness of the membrane 28 is approximately no less than 1/3 of the diameter of the membrane 28.

The assembly 10 is fabricated from a single piece of medical grade elastomeric material. In an embodiment, the elastomeric material is a silicone elastomer. Silicone elastomer has strong memory or rebound characteristics, may be sterilized, and is biocompatible. In a particular embodiment, the silicone elastomer is translucent. The translucent characteristic of the silicone elastomer may aid a user of the assembly 10 during a medical procedure. For example, in certain situations the user may be removing a piece of biopsy tissue or a polyp from the uterus of a patient. After the tissue or the polyp is removed from the uterus, the tissue will need to be retrieved from the patient by passing the tissue or polyp back out through the assembly 10. The translucent characteristic of the assembly 10 will allow the user to easily find, locate and remove the tissue or polyp from the assembly 10, thus minimizing a common complication of existing seals, where the tissue or polyp becomes "lost" in the seal. Additionally, the translucency of the assembly 10 allows the user to clearly visualize the angle of the auxiliary instrument as the instrument penetrates the assembly 10. This will decrease undesirable positioning which may lead to damage of the auxiliary instrument. In an embodiment, the translucent silicone elastomer is Silastic® which is manufactured by Dow Corning Corporation and is approximately 50 durometer Shore A. In an embodiment, the assembly 10 is designed to be water tight under pressure no greater than about 100 mmHg. In an embodiment, the membrane 28 of the assembly 10 may be punctured with a blunt obturator prior to use.

Typical prior art seals are not disposable, and must be taken apart and cleaned between uses. This adds to the difficulty of carrying out an endoscopic diagnosis and adds significantly to the cost of examination. Also, a non-disposable seal that is not sterilized properly may introduce bacteria and other harmful agents to a patient, and therefore the risk of cross-contamination between patients is high. The assembly 10 of the present disclosure is provided for single-use, and therefore is made to be disposable.

Figure 2A:
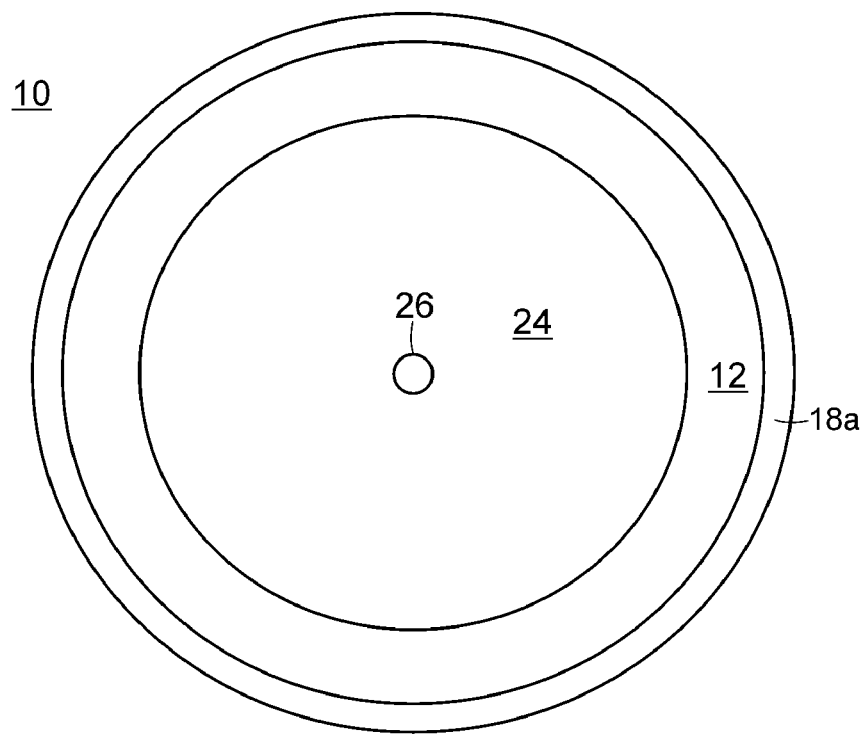
FIGS. 2A and 2B show an embodiment of a self-sealing assembly of the present disclosure.
Figure 2B:
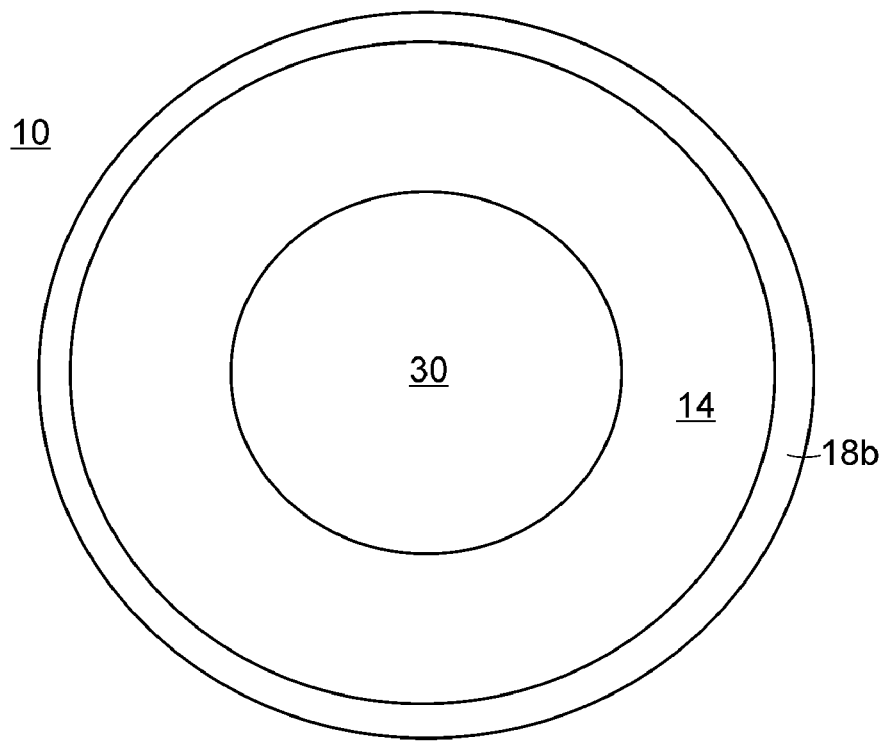

FIG. 2A shows a top view looking at the proximal end 12 of the assembly 10. As seen in FIG. 2A, the diameter of the stem portion 26 is much smaller than the initial diameter of the conical mouth 24, allowing for a user to efficiently introduce the auxiliary instrument into the assembly 10. The wide conical mouth 24 allows for the auxiliary instrument to "self-introduce" into the assembly 10. The proximal lip 18a of the middle region 17 is also visible from this view. FIG. 2B shows a bottom view looking at the distal end 14 of the assembly 10. In this view, the transfer section 30 is visible, as is the distal lip 18b of the middle region 17. The transfer section 30 is able to accommodate various types of fittings that may be present on the inlet port of the medical device, such as, for example, a Luer-lock fitting or a ball-and-socket fitting. A major deficiency in the seal plugs in the art is the lack of adaptability of such devices to endoscopes and hysteroscopes that typically include anything other than a flat ended sheath at the accessory channel port. However, many endoscopes and hysteroscopes typically instead include a ball-and-socket fitting at the accessory channel port to provide flexibility and maneuverability to the auxiliary instrument when it is introduced into the endoscope or hysteroscope. It is at this ball-and-socket fitting that fluid might escape if an improper seal is provided. Because the transfer section 30 of the assembly 10 of the presently disclosed embodiments is made from an elastomeric material, it may be stretched to accommodate various types of adaptors. The properties of the elastomeric material allow the transfer section 30 to stretch to fit around the adaptor or around the inlet port of the accessory channel.

Figure 3A:
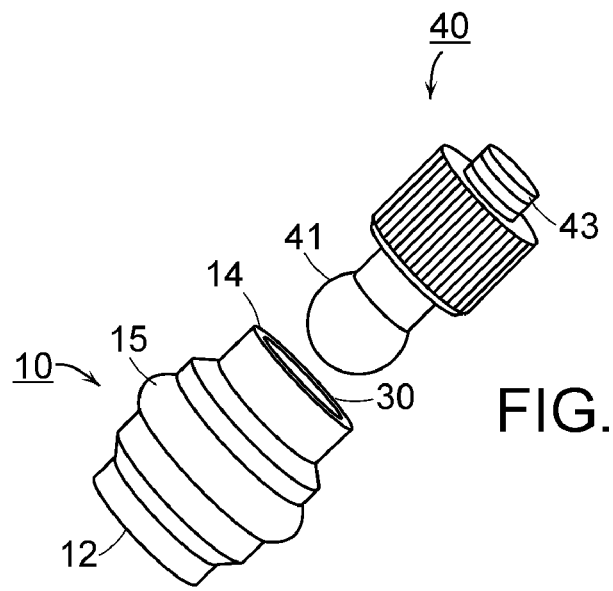
FIGS. 3A, 3B and 3C show an embodiment of a self-sealing assembly of the present disclosure being engaged to a Luer-lock adaptor.
Figure 3B:
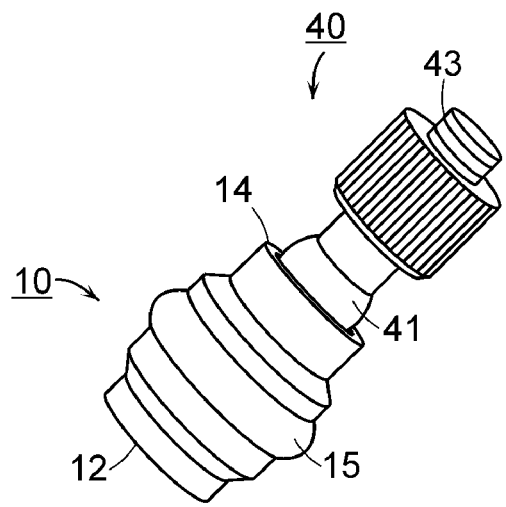
Figure 3C:
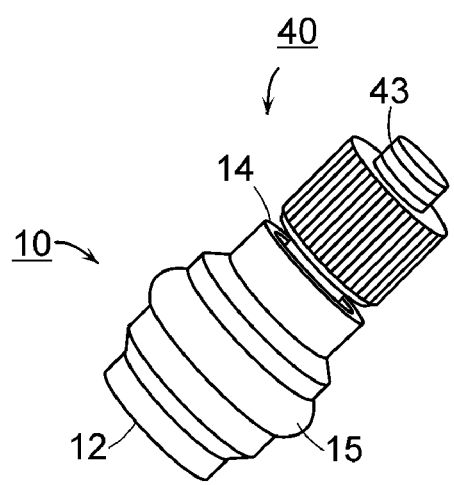
Figure 4A:
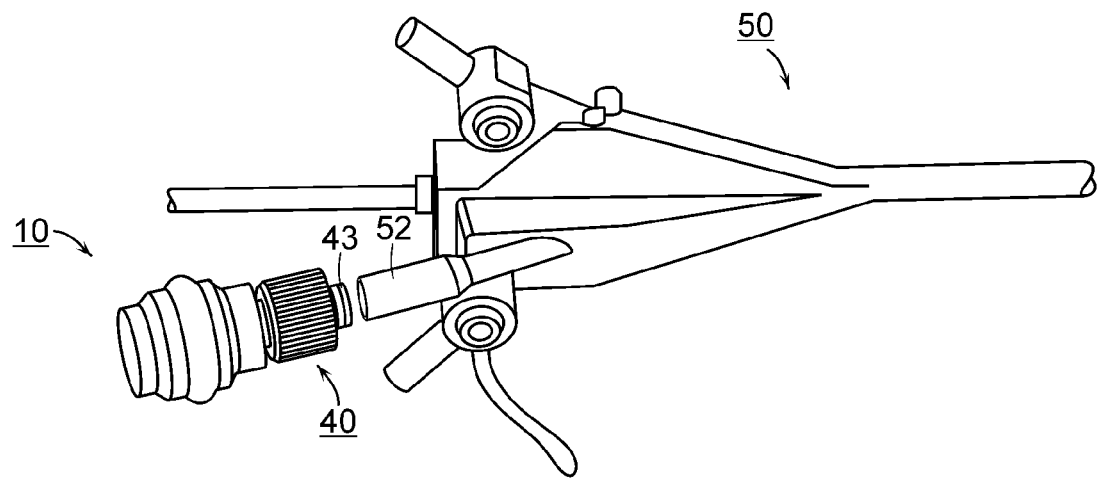
FIGS. 4A and 4B show an embodiment of the self-sealing assembly of FIG. 3C being engaged to a Luer-lock fitted accessory channel on a hysteroscope.
Figure 4B:
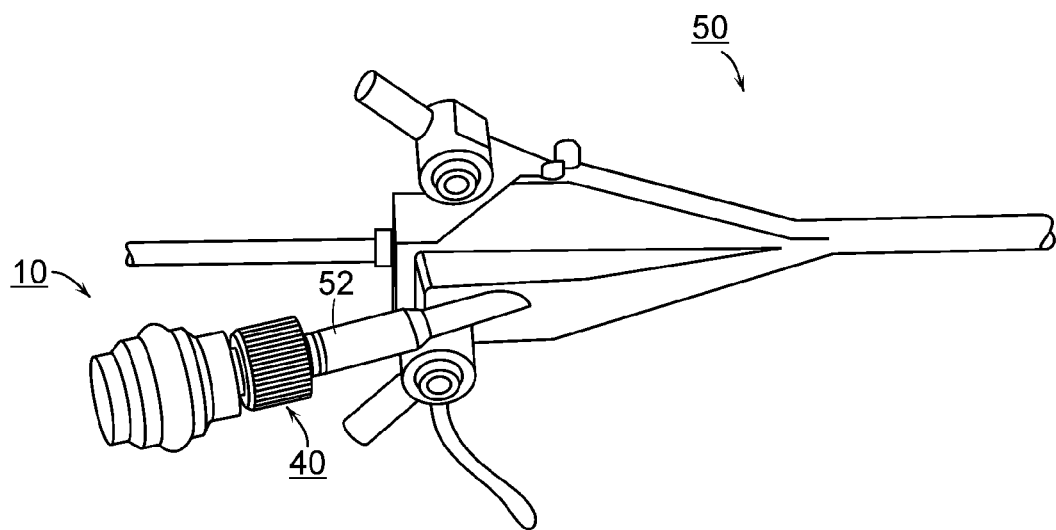
Figure 5A:
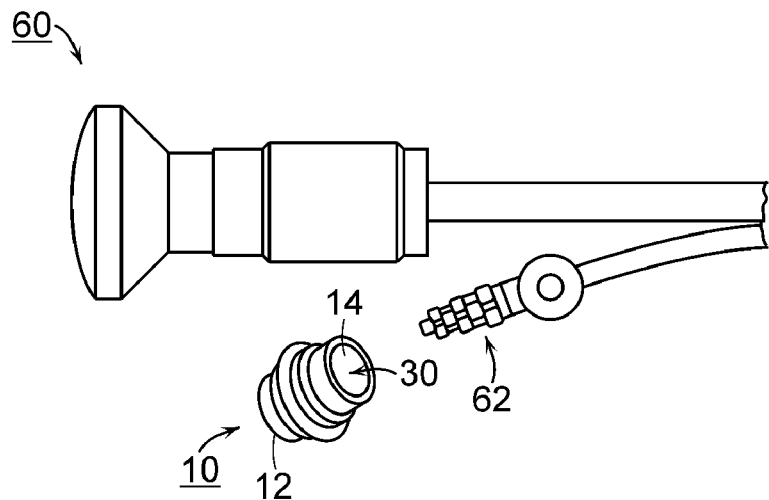
FIGS. 5A, 5B and 5C show an embodiment of a self-sealing assembly of the present disclosure being engaged to a Luer-lock fitted accessory channel on a hysteroscope.
Figure 5B:
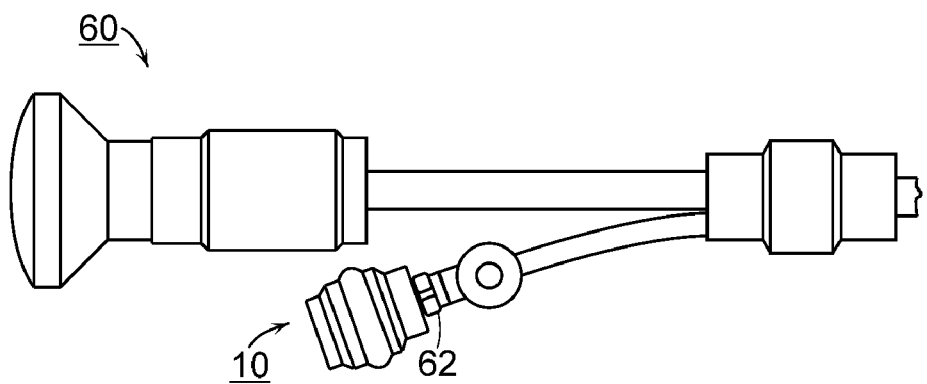
Figure 5C:
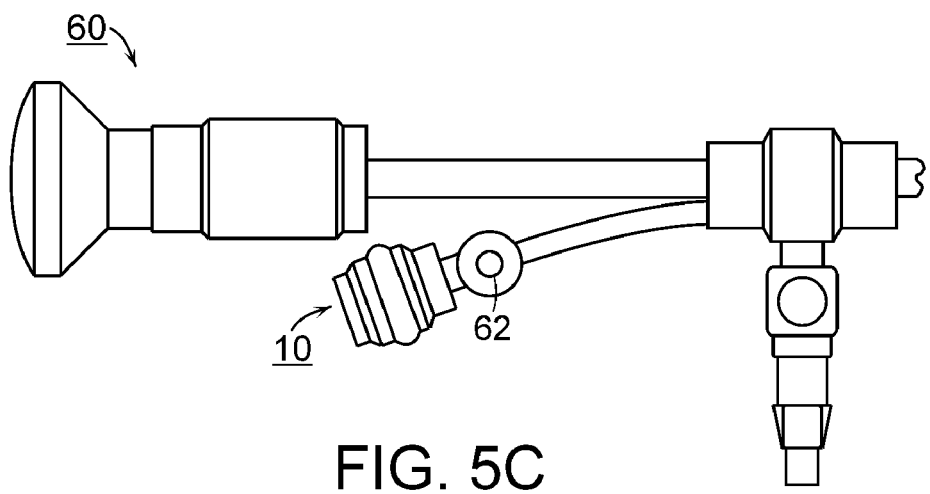

During a medical procedure, a user will engage the assembly 10 either to a Luer-lock adaptor for connection to a Luer-lock fitted accessory channel of a medical device, or alternatively directly to a traditional accessory channel of the medical device, such as a ball end adaptor fitted accessory channel. As shown in FIGS. 3A, 3B and 3C, an assembly 10 is being engaged to a Luer-lock adaptor 40 having a port 41 and a lock 43. The assembly 10 has an elastic band 15 wrapped around the cavity 19. The elastic band 15 helps a user of the assembly 10 to visually determine the measurement of the diameter of the stem portion 26. For example, in an embodiment the elastic band 15 is orange, which represents a 0.6 mm diameter stem portion 26. In an embodiment, the elastic band 15 is teal, which represents a 1.2 mm diameter stem portion 26. The transfer section 30 is able to accommodate the port 41 on the Luer-lock adaptor 40. The port 41 is squeezed into the transfer section 30 of assembly 10, such that the Luer-lock adaptor 40 has a snug fit with the transfer section 30. A hole in the port 41 surrounds the membrane 28 of the assembly 10 such that an auxiliary instrument that passes through the membrane 28 can easily pass into the port 41 of the Luer-lock adaptor 40. As shown in FIGS. 4A and 4B, the assembly 10 engaged to the Luer-lock adaptor 40 is being attached to a Luer-lock fitted accessory channel 52 on a hysteroscope 50. Briefly, the lock 43 of the Luer-lock adaptor 40 is slid over the Luer-lock fitted accessory channel 52 and turned clockwise until the Luer-lock adaptor 40 is locked into place. The Luer-lock adaptor 40 can be pulled back slightly to confirm that the Luer-lock adaptor 40 is locked into place on the Luer-lock fitted accessory channel 52 of the hysteroscope 50. As shown in the embodiment depicted in FIGS. 5A, 5B and 5C, the assembly 10 may be attached directly to a ball end adaptor fitted accessory channel 62 on a hysteroscope 60. Briefly, the transfer section 30 of assembly 10 is placed directly onto the ball end adaptor fitted accessory channel 62. The assembly 10 is pushed onto the ball end adaptor fitted accessory channel 62 until a tight fit is confirmed, by pulling on the assembly 10 to make sure that the assembly 10 has a snug fit.

An auxiliary instrument may be introduced into the introducer section 20 of the assembly 10 and moved from the wide mouth portion 24 through the narrow stem portion 26 until it reaches the membrane 28. As an instrument moves through the stem portion 26, the instrument is being squeezed and guided by the narrow stem portion 26, providing complete contact between the instrument and the stem portion 26 throughout the entire length of the stem portion 26. When the instrument reaches the membrane 28, a slight resistance will be felt by the user. Pressure exerted by the instrument on the membrane 28, results in the stretching of the membrane 28 in a direction from the proximal end 32 of the transfer section 30 towards the distal end 34 of the transfer section 30. The stretched membrane 28 surrounds at least a portion of the instrument and when sufficient pressure is exerted on the membrane 28 by the instrument, a hole is created in the membrane 28. The instrument passes through the hole in the membrane 28, enters the proximal end 32 of the transfer section 30, followed by passing through the distal end 34. The instrument may then enter into the accessory channel of the medical device. The membrane 28 and the stem portion 26 squeeze and surround the auxiliary instrument resulting in a fluid-seal around the auxiliary instrument. The elastomeric assembly with the desired thickness membrane 28, and desired length stem portion 26 help ensure a tight, snug and solid fluid-seal around the auxiliary instrument. Even if the user manipulates the auxiliary instrument during the procedure, the membrane 28, which extends from the stem portion 26, will move with the stem portion 26 and the fluid-seal will remain.

The stem portion 26 and the membrane 28 squeeze the instrument and provide multiple points of contact with the instrument such that any movement that the instrument makes, the membrane 28 and the stem portion 26 will mimic along. This "mimicking" of the membrane 28 and the stem portion 26 to the movements of the instrument are necessary for maintaining the fluid-seal. Without being limited to any particular theory, there are a number of unique features of the assembly 10 that makes this mimicking possible. The length of the stem portion 26 is chosen such that the stem portion 26 guides the instrument towards a center of the membrane 28. The membrane 28 extends from the stem portion 26 such that any lateral movement imparted on the stem portion 26 by the auxiliary instrument will be transferred to the membrane 28 such that the center of the membrane 28 is always aligned with a center of the auxiliary instrument. This "floating membrane" design insures leakage is prevented during any lateral movement by the auxiliary instrument. The diameter of the stem portion 26 is chosen such that instrument remains in contact with and is squeezed by the stem portion 26 along the entire length of the stem portion 26. The flexible elastomeric material that the stem portion 26 and the membrane 28 are fabricated from provide maneuverability to the stem portion 26 and the membrane 28. This maneuverability allows the stem portion 26 and the membrane 28 to move along with the instrument during the procedure. The thickness of the membrane 28 is chosen such that the membrane 28 will puncture when pressure is applied to the membrane 28 by the instrument. The membrane 28 stretches and surrounds the instrument until a peak pressure is achieved which causes the instrument to penetrate the membrane 28.

When the auxiliary instrument no longer is needed for the medical procedure, the instrument can be taken out of the assembly 10 without the need to worry whether the assembly will maintain a fluid or a gas seal. The stem portion 26 directs the instrument out of the assembly 10 and prevents an angled penetration when the instrument is removed. When the auxiliary instrument is pulled back through the membrane 28 and the stem portion 26, the hole that was created in the membrane 28 rebounds back such that the membrane 28 returns substantially to the original shape. The ratio of the thickness of the membrane 28 to the diameter of the membrane 28 is chosen such that the membrane 28 substantially returns to the original shape even under fluid or gas pressure, maintaining a fluid-seal even when the instrument is no longer within the assembly 10.

The self-sealing assemblies 10 of the present disclosure may be used, in an embodiment, during a hysteroscopy procedure. During a hysteroscopy procedure, a hysteroscope, a thin telescope, is inserted through the cervix into the uterus. In an embodiment, a self-sealing assembly 10 is used during a diagnostic hysteroscopy procedure. In an embodiment, a self-sealing assembly 10 is used during an operative hysteroscopy procedure. The hysteroscope used for operative hysteroscopy typically includes at least one channel in which it is possible to insert auxiliary instruments for operative purposes, such as a biopsy of uterine tissue or the removal of a polyp. A self-sealing assembly 10 of the present disclosure may be used during an operative hysteroscopy procedure. The self-sealing assembly 10 is capable of minimizing the backflow of non-viscous uterine distention fluid when there is either no auxiliary instrument being used in the assembly 10, when there is an auxiliary instrument within the assembly 10, and after the auxiliary instrument has been withdrawn from the assembly 10.

A method for performing an operative hysteroscopy procedure includes connecting an self-sealing assembly to an operative channel of a hysteroscope, wherein the self-sealing assembly comprises an introducer section, a transfer section, and a membrane therebetween, wherein the introducer section is approximately funnel-shaped, having a first portion, a second portion, and a longitudinal axis therebetween, wherein the first portion has a gradually decreasing diameter over a first length, and wherein the second portion has a substantially constant diameter over a second length, wherein the membrane is fabricated from a single piece translucent elastomeric material having a thickness such that the membrane is capable of stretching when pressure is applied to the membrane by an auxiliary instrument, and wherein the transfer section of the self-sealing assembly is attached to the operative channel of the hysteroscope; numbing a cervix of a subject using an anesthetic; inserting the hysteroscope into a uterus of the subject; distending the uterus with either liquid or gaseous media; inserting the auxiliary instrument into the first portion of the self-sealing assembly; pushing the auxiliary instrument through the first portion and into the second portion of the self-sealing assembly until the auxiliary instrument reaches the membrane; pressurizing the membrane with the auxiliary instrument such that the membrane stretches in a direction from a proximal end of the transfer section towards a distal end of the transfer section; surrounding at least a portion of the auxiliary instrument with the membrane as the auxiliary instrument puts pressure on the membrane; creating a hole in the membrane such that the auxiliary instrument passes through the membrane and into the transfer section, wherein an inner surface of the hole created in the membrane engages the auxiliary instrument resulting in a fluid-seal around the auxiliary instrument; moving the auxiliary instrument through the operative channel until the auxiliary instrument reaches the uterus, wherein the auxiliary instrument remains surrounded by the membrane, and wherein the membrane mimics the movement of the auxiliary instrument as the user manipulates the auxiliary instrument within the operative channel; performing the hysteroscopy procedure; pulling the auxiliary instrument back through the self-sealing assembly, wherein when the auxiliary instrument is pulled back through the membrane and into the introducer section, the hole created in the membrane relaxes so that the hole is substantially closed resulting in a fluid-seal; and removing the hysteroscope from the uterus. The method for performing the operative hysteroscopy procedure prevents (substantially minimizes) the backflow of non-viscous uterine distention fluid.

A method for establishing a fluid-seal around a medical instrument includes providing a medical device having an accessory channel; attaching an assembly to the accessory channel of the medical device, wherein the assembly comprises an introducer section, a transfer section, and a self-sealing membrane therebetween, wherein the introducer section is approximately funnel-shaped, having a first portion, a second portion, and a longitudinal axis therebetween, wherein the first portion has a gradually decreasing diameter over a first length, and wherein the second portion has a substantially constant diameter over a second length, wherein the self-sealing membrane is fabricated from a single piece flexible elastomeric material having a thickness such that the self-sealing membrane is capable of stretching when pressure is applied to the self-sealing membrane, and wherein the transfer section is attached to the accessory channel of the medical device; introducing the medical instrument into the introducer section of the assembly such that the medical instrument moves through the first portion and into the second portion, wherein the first portion guides the medical instrument into the second portion, and wherein the second portion contacts and squeezes the medical instrument as the medical instrument passes through the length of the second portion; exerting pressure on the self-sealing membrane by the medical instrument resulting in the self-sealing membrane stretching in a direction from a proximal end of the transfer section towards a distal end of the transfer section; surrounding at least a portion of the medical instrument with the self-sealing membrane as the medical instrument puts pressure on the self-sealing membrane; and creating a hole in the self-sealing membrane such that the medical instrument passes through the self-sealing membrane and into the transfer section, wherein an inner surface of the hole created in the self-sealing membrane engages the medical instrument resulting in the fluid-seal around the medical instrument.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An assembly for providing resistance to fluid leakage comprising:
    an introducer section having a mouth portion, a stem portion, and a longitudinal axis therebetween,
        wherein a diameter of the mouth portion decreases over a length of the mouth portion, and
        wherein a diameter of the stem portion remains substantially the same over a length of the stem portion;
    a transfer section having a proximal end and a distal end; and
    a self-sealing membrane at a junction between the stem portion and the proximal end of the transfer section,
        wherein the self-sealing membrane is composed of a single piece flexible elastomeric material having a conical shape protruding into the transfer section,
        wherein the self-sealing membrane is fully in-tact prior to the introduction of an auxiliary instrument through the self-sealing membrane, and
        wherein the fully in-tact self-sealing membrane has a thickness such that the self-sealing membrane stretches into the transfer section after pressure is exerted on the self-sealing membrane by the auxiliary instrument, and
    wherein the diameter and the length of the stem portion and a ratio of the thickness to a diameter of the self-sealing membrane are configured to provide structural integrity to the assembly resulting in the ability of the self-sealing membrane to resist fluid leakage prior to, during, and after the self-sealing membrane is punctured.

2. The assembly of claim 1 wherein the introducer section is approximately funnel-shaped.

3. The assembly of claim 1 wherein the introducer section, the transfer section and the self-sealing membrane are fabricated using a single piece of elastomeric material.

4. The assembly of claim 3 wherein the elastomeric material is a translucent silicone elastomer.

5. The assembly of claim 1 wherein the length of the stem portion is in a range of about 3 mm to about 4 mm.

6. The assembly of claim 1 wherein the diameter of the stem portion is in a range of about 0.6 mm to about 3 mm.

7. The assembly of claim 1 wherein the thickness of the self-sealing membrane is in a range of about 0.3 mm to about 2 mm.

8. The assembly of claim 1 wherein the transfer section is capable of engaging to at least one of a Luer-lock adaptor, a ball-in-socket adaptor, or a Tuohy Borst adaptor.

9. The assembly of claim 1 wherein a hole is created in the self-sealing membrane by the auxiliary instrument.

10. The assembly of claim 9 wherein the hole created in the self-sealing membrane results in the auxiliary instrument passing through the self-sealing membrane and into the transfer section.

11. The assembly of claim 10 wherein the self-sealing membrane surrounds the auxiliary instrument as the instrument passes through the self-sealing membrane resulting in a fluid-seal around the auxiliary instrument.

12. The assembly of claim 11 wherein the self-sealing membrane extends from the stem portion such that any lateral movement imparted by the auxiliary instrument to the stem portion is transferred to the self-sealing membrane, resulting in the self-sealing membrane remaining centered on the auxiliary instrument and providing the fluid-seal.

13. The assembly of claim 11 wherein when the auxiliary instrument is passed back through the self-sealing membrane and into the introducer section, the hole created in the self-sealing membrane relaxes so that the perforation is substantially closed resulting in a seal.

14. The assembly of claim 11 wherein the ratio of the thickness of the self-sealing membrane to the diameter of the self sealing membrane is chosen such that when the auxiliary instrument is passed back through the self-sealing membrane and into the introducer section the self sealing membrane remains substantially closed even if fluid or gas pressure is present in the assembly.

15. An assembly for providing resistance to fluid backflow comprising:
an outer circumferential surface having a proximal end, a distal end, and a middle region therebetween,
wherein the outer circumferential surface of the middle region includes a proximal lip, a distal lip, and a cavity therebetween,
wherein an elastic band is wrapped around the outer circumferential surface of the cavity; and
an inner body having an introducer section, a transfer section, and a self-sealing membrane therebetween,
wherein the introducer section is approximately funnel-shaped, having a first portion, a second portion, and a longitudinal axis therebetween,
wherein a diameter of the first portion decreases over a first length, and wherein a diameter of the second portion remains substantially the same over a second length, and wherein the diameter of the second portion is represented by a color of the elastic band wrapped around the outer circumferential surface of the cavity,
wherein the transfer section has a proximal end, a distal end, and a longitudinal axis therebetween, and
wherein the self-sealing membrane is composed of a fully in-tact single piece flexible elastomeric material prior to the introduction of an auxiliary instrument through the self-sealing membrane, and wherein the fully in-tact self-sealing membrane has a thickness such that the fully in-tact self-sealing membrane extends from the second portion of the introducer section into the transfer section when pressure is applied to the fully in-tact self-sealing membrane by the auxiliary instrument and before being pierced by the auxiliary instrument.

16. The assembly of claim 15 wherein the pressure applied to the self-sealing membrane causes the self-sealing membrane to stretch in a direction from the proximal end of the transfer section towards the distal end of the transfer section,
wherein the self-sealing membrane surrounds at least a portion of the medical instrument as the self-sealing membrane is stretched,
wherein a hole having a diameter is created in the self-sealing membrane resulting in the medical instrument passing through the self-sealing membrane and into the transfer section,
wherein the self-sealing membrane surrounds the medical instrument as the medical instrument passes through the self-sealing membrane resulting in a fluid-seal around the medical instrument, and
wherein the diameter and the length of the second portion and the thickness of the self-sealing membrane provide structural integrity to the assembly resulting in the ability of the self-sealing membrane to resist fluid backflow after the medical instrument is removed from the assembly.

17. A method for establishing a fluid-seal around a medical instrument comprising:
attaching an assembly to an accessory channel of a medical device, wherein the assembly comprises an introducer section, a transfer section, and a fully in-tact self-sealing membrane therebetween,
wherein the introducer section is approximately funnel-shaped, having a first portion, a second portion, and a longitudinal axis therebetween,
wherein a diameter of the first portion decreases over a first length, and
wherein a diameter of the second portion remains substantially the same over a second length,
wherein the fully in-tact self-sealing membrane is composed of a single piece flexible elastomeric material having a semi-spherical shape protruding into the transfer section,
wherein a thickness of the fully in-tact self-sealing membrane is no less than approximately $\frac{1}{5}$ of a diameter of the fully in-tact self-sealing membrane, and
wherein the transfer section is attached to the accessory channel of the medical device;
introducing the medical instrument into the introducer section of the assembly such that the first portion guides the medical instrument into the second portion, and the second portion contacts and squeezes the medical instrument as the medical instrument passes through the length of the second portion;
exerting pressure on the fully in-tact self-sealing membrane by the medical instrument, wherein the thickness of the fully in-tact self-sealing membrane is configured to stretch the fully in-tact self-sealing membrane in a direction from a proximal end of the transfer section towards a distal end of the transfer section; and
creating a hole in the fully in-tact self-sealing membrane such that the medical instrument engages an entire inner surface of the hole as the medical instrument passes through the hole in the self-sealing membrane and into the transfer section, resulting in the fluid-seal around the medical instrument.

18. The assembly of claim 15 wherein the thickness of the self-sealing membrane ranges from about 0.3 mm to about 2 mm.

19. The assembly of claim 15 wherein the diameter of the second portion is in a range of about 0.6 mm to about 3 mm.

20. The assembly of claim 15 wherein the thickness of the self-sealing membrane is no less than approximately $\frac{1}{5}$ of a diameter of the self-sealing membrane.

* * * * *